United States Patent
He et al.

(10) Patent No.: US 12,329,794 B2
(45) Date of Patent: Jun. 17, 2025

(54) RECOMBINANT HERPES SIMPLEX VIRUS FOR CANCER IMMUNOTHERAPY

(71) Applicant: THE BOARD OF TRUSTEES OF THE UNIVERSITY OF ILLINOIS, Urbana, IL (US)

(72) Inventors: Bin He, Chicago, IL (US); Xing Liu, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1017 days.

(21) Appl. No.: 17/054,338

(22) PCT Filed: Jun. 7, 2019

(86) PCT No.: PCT/US2019/035922
§ 371 (c)(1),
(2) Date: Nov. 10, 2020

(87) PCT Pub. No.: WO2019/236931
PCT Pub. Date: Dec. 12, 2019

(65) Prior Publication Data
US 2021/0138009 A1    May 13, 2021

Related U.S. Application Data

(60) Provisional application No. 62/682,202, filed on Jun. 8, 2018.

(51) Int. Cl.
| | |
|---|---|
| *A61K 35/763* | (2015.01) |
| *A61P 35/00* | (2006.01) |
| *A61P 35/04* | (2006.01) |
| *C12N 7/00* | (2006.01) |
| *C12N 15/09* | (2006.01) |
| *C12N 15/63* | (2006.01) |

(52) U.S. Cl.
CPC ............ *A61K 35/763* (2013.01); *A61P 35/00* (2018.01); *A61P 35/04* (2018.01); *C12N 7/00* (2013.01); *C12N 15/09* (2013.01); *C12N 15/63* (2013.01); *C12N 2710/16621* (2013.01); *C12N 2710/16632* (2013.01)

(58) Field of Classification Search
CPC ........ A61K 35/763; A61P 35/04; A61P 35/00; C12N 7/00; C12N 15/09; C12N 15/63; C12N 2710/16621; C12N 2710/16632
See application file for complete search history.

(56) References Cited

U.S. PATENT DOCUMENTS

| | | |
|---|---|---|
| 2003/0091537 A1 | 5/2003 | Coffin |
| 2008/0069837 A1* | 3/2008 | Nishiyama ............ A61K 31/337 424/199.1 |
| 2010/0272691 A1 | 10/2010 | Conner |
| 2017/0319638 A1 | 11/2017 | Conner et al. |

FOREIGN PATENT DOCUMENTS

| | | |
|---|---|---|
| WO | 2017013419 A1 | 1/2017 |
| WO | 2017013421 A1 | 1/2017 |

OTHER PUBLICATIONS

Ma Y, Chen M, Jin H, Prabhakar BS, Valyi-Nagy T, He B. An Engineered Herpesvirus Activates Dendritic Cells and Induces Protective Immunity. Sci Rep. Feb. 2, 2017;7:41461. (Year: 2017).*
Kanai R, Zaupa C, Sgubin D, Antoszczyk SJ, Martuza RL, Wakimoto H, Rabkin SD. Effect of γ34.5 deletions on oncolytic herpes simplex virus activity in brain tumors. J Virol. Apr. 2012;86(8):4420-31. (Year: 2012).*
Krisky DM, Marconi PC, Oligino TJ, Rouse RJ, Fink DJ, Cohen JB, Watkins SC, Glorioso JC. Development of herpes simplex virus replication-defective multigene vectors for combination gene therapy applications. Gene Ther. Nov. 1998;5(11):1517-30. (Year: 1998).*
Emanuele Sasso.Generation and in vitro characterization of cancer immunotherapeutics based on oncolytic viruses and immune checkpoint inhibitors. University of Naples Federico II, Ph.D. in Medicine, Medical Molecular and Biotechnology. 2016 (Year: 2016).*
Toyoizumi T, Mick R, Abbas AE, Kang EH, Kaiser LR, Molnar-Kimber KL. Combined therapy with chemotherapeutic agents and herpes simplex virus type 1 ICP34.5 mutant (HSV-1716) in human non-small cell lung cancer. Hum Gene Ther. Dec. 10, 1999; 10(18):3013-29. (Year: 1999).*
Parker BS, Rautela J, Hertzog PJ. Antitumour actions of interferons: implications for cancer therapy. Nat Rev Cancer. Mar. 2016;16(3):131-44. (Year: 2016).*
Ma Y, Jin H, Valyi-Nagy T, Cao Y, Yan Z, He B. Inhibition of TANK binding kinase 1 by herpes simplex virus 1 facilitates productive infection. J Virol. Feb. 2012;86(4):2188-96. doi: 10.1128/JVI.05376-11. Epub Dec. 14, 2011. (Year: 2012).*
Veerapong J, Bickenbach KA, Shao MY, Smith KD, Posner MC, Roizman B, Weichselbaum RR. Systemic delivery of (gamma1) 34.5-deleted herpes simplex virus-1 selectively targets and treats distant human xenograft tumors that express high MEK activity. Cancer Res. Sep. 1, 2007;67(17):8301-6. (Year: 2007).*
Szpara ML, Parsons L, Enquist LW. Sequence variability in clinical and laboratory isolates of herpes simplex virus 1 reveals new mutations. J Virol. May 2010;84(10):5303-13. (Year: 2010).*
Official Communication dated Nov. 26, 2021 from EP 19733912.0 filed Jun. 7, 2019.

(Continued)

*Primary Examiner* — Nicole Kinsey White
*Assistant Examiner* — Ruixue Wang
(74) *Attorney, Agent, or Firm* — Licata & Tyrrell P.C.; Jane Massey Licata

(57) ABSTRACT

A method for treating a subject with cancer by administering to the subject a therapeutically effective amount of a recombinant Herpes Simplex Virus-1 (HSV-1) that expresses only a C-terminal portion of $\gamma_1 34.5$ protein (e.g., amino acid residues 147-263) with no wild-type or intact $\gamma_1 34.5$ protein expression is provided. The recombinant HSV-1 of this invention instigates immune activation, selectively replicates in cancer cells, and resists clearance by interferon.

8 Claims, 3 Drawing Sheets

Specification includes a Sequence Listing.

(56) References Cited

OTHER PUBLICATIONS

Andtbacka, R.H.I, et al. (2015) "Talimogene Laherparepvec Improves Durable Response Rate in Patients with Advanced Melanoma," J. Clin. Oncol. 33(25):2780-88.

Braidwood, L., et al. (2014) "Potent efficacy signals from systemically administered oncolytic herpes simplex virus (HSV1716) in hepatocellular carcinoma xenograft models," J. Hepatocell. Carcinoma 1:149-61.

Chambers, R., et al. (1995) "Comparison of genetically engineered herpes simplex viruses for the treatment of brain tumors in a scid mouse model of human malignant glioma," Proc. Natl. Acad. Sci . USA 92(5):1411-15.

Coukos, G., et al. (2000) "Oncolytic Herpes Simplex Virus-1 Lacking ICP34.5 Induces p53-Independent Death and is Efficacious against Chemotherapy Chemotherapy-resistant Ovarian Cancer," Clin. Cancer Res. 6:3342-53.

Fukuhara, H. et al. (2016) "Oncolytic virus therapy: A new era of cancer treatment at dawn," Cancer Sci. 107(10):1373-79.

International Preliminary Report on Patentability in PCT/US2019/035922 dated Dec. 8, 2020.

International Search Report and Written Opinion in PCT/US2019/035922 dated Aug. 16, 2019.

Ma, Y., et al. (2012) "Inhibition of TANK Binding Kinase 1 by Herpes Simplex Virus 1 Facilitates Productive Infection," J. Virol. 86:2188-2196.

Ma, Y., et al (2017) "An Engineered Herpesvirus Activates Dendritic Cells and Induces Protective Immunity," Sci. Rep. 7:41461.

Markert, J.M., et al. (2000) "Conditionally replicating herpes simplex virus mutant, G207 for the treatment of malignant glioma: results of a phase I trial," Gene Ther. 7(10):867-74.

Pan, S., et al.(2018) "Herpes Simplex Virus 1 gamma134.5 Protein Inhibits STING Activation That Restricts Viral Replication," J. Virol. 92(20):e01015-18.

Peters, C., & Rabkin, S.D. (2015) "Designing Herpes Viruses as Oncolytics," Mol. Ther. Oncolytics 2:15010.

Randazzo, B.P., et al. (1995) "Treatment of experimental intracranial murine melanoma with a neuro-attenuated Herpes Simpex virus-1 mutant," Virology 211: 94-101.

Streby, K.A., et al. (2017) "Intratumoral Injection of HSV1716, an Oncolytic Herpes Virus, is Safe and Shows Evidence of Immune Response and Viral Replication in Young Cancer Patients," Clin. Cancer Res. 23(14):3566-74.

Thomas. D.L. & Fraser, N.W. (2003) "HSV-1 therapy of primary tumors reduces the number of metastases in an Immune-competent model of metastatic breast cancer," Mol. Ther. 8:543-51.

\* cited by examiner

SEQUENCE LISTING

<160> NUMBER OF SEQ ID NOS: 22

<210> SEQ ID NO 1
<211> LENGTH: 248
<212> TYPE: PRT
<213> ORGANISM: herpes simplex virus 1

<400> SEQUENCE: 1

```
Met Ala Arg Arg Arg His Arg Gly Pro Arg Arg Pro Arg Pro Pro
1               5                   10                  15

Gly Pro Thr Gly Ala Val Pro Thr Ala Gln Ser Gln Val Thr Ser Thr
                20                  25                  30

Pro Asn Ser Glu Pro Ala Val Arg Ser Ala Pro Ala Ala Ala Pro Pro
            35                  40                  45

Pro Pro Pro Ala Ser Gly Pro Pro Ser Cys Ser Leu Leu Leu Arg
    50                  55                  60

Gln Trp Leu His Val Pro Glu Ser Ala Ser Asp Asp Asp Asp Asp
65                  70                  75                  80

Asp Trp Pro Asp Ser Pro Pro Glu Pro Ala Pro Glu Ala Arg Pro
                85                  90                  95

Thr Ala Ala Ala Pro Arg Pro Arg Ser Pro Pro Pro Gly Ala Gly Pro
                100                 105                 110

Gly Gly Gly Ala Asn Pro Ser His Pro Pro Ser Arg Pro Phe Arg Leu
            115                 120                 125

Pro Pro Arg Leu Ala Leu Arg Leu Arg Val Thr Ala Glu His Leu Ala
        130                 135                 140

Arg Leu Arg Leu Arg Arg Ala Gly Gly Glu Gly Ala Pro Glu Pro Pro
145                 150                 155                 160

Ala Thr Pro Ala Thr Pro Ala Thr Pro Ala Thr Pro Ala Thr Pro Ala
                165                 170                 175
```

Arg Val Arg Phe Ser Pro His Val Arg Val His Leu Val Val Trp
            180                 185                 190

Ala Ser Ala Ala Arg Leu Ala Arg Arg Gly Ser Trp Ala Arg Glu Arg
        195                 200                 205

Ala Asp Arg Ala Arg Phe Arg Arg Val Ala Glu Ala Glu Ala Val
    210                 215                 220

Ile Gly Pro Cys Leu Gly Pro Glu Ala Arg Ala Arg Ala Leu Ala Arg
225                 230                 235                 240

Gly Ala Gly Pro Ala Asn Ser Val
                245

<210> SEQ ID NO 2
<211> LENGTH: 102
<212> TYPE: PRT
<213> ORGANISM: Artificial sequence
<220> FEATURE:
<223> OTHER INFORMATION: Synthetic polypeptide

<400> SEQUENCE: 2

Arg Leu Arg Arg Ala Gly Gly Glu Gly Ala Pro Glu Pro Pro Ala Thr
1               5                   10                  15

Pro Ala Thr Pro Ala Thr Pro Ala Thr Pro Ala Thr Pro Ala Arg Val
            20                  25                  30

Arg Phe Ser Pro His Val Arg Val His Leu Val Val Trp Ala Ser
        35                  40                  45

Ala Ala Arg Leu Ala Arg Arg Gly Ser Trp Ala Arg Glu Arg Ala Asp
    50                  55                  60

Arg Ala Arg Phe Arg Arg Val Ala Glu Ala Glu Ala Val Ile Gly
65                  70                  75                  80

Pro Cys Leu Gly Pro Glu Ala Arg Ala Arg Ala Leu Ala Arg Gly Ala
                85                  90                  95

Gly Pro Ala Asn Ser Val
            100

<210> SEQ ID NO 3
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 3
gccttgacac tcctggtaca aatgag                                        26

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 4
cagcacattg gcagaggaag acag                                          24

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
caaggcaggt ttctgaggag                                               20

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 6
aagcagattc tccatgacct g                                             21

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
ctgctgcttt gcctacctct                                               20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
cacttcttct ctgggttggc                                               20

<210> SEQ ID NO 9
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 9
tccttccttc cttccttcct tcc                                           23

<210> SEQ ID NO 10
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 10
aggctctttt tcaccctgtc tgg                                           23

<210> SEQ ID NO 11
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 11
ggccttgacc tttgctttac tg                                            22

<210> SEQ ID NO 12
<211> LENGTH: 21

```
<212> TYPE: DNA
<213> ORGANISM: Artificial sequence
<220> FEATURE:
<223> OTHER INFORMATION: Synthetic oligonucleotide

<400> SEQUENCE: 12
cacagagcag cttgacttgc a                                             21

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
cctccttggg ttcgtctaca                                               20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
agtggctgat atctgggtgc                                               20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
cctgctgctt tgcctacatt                                               20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
acacacttgg cggttctttc                                               20

<210> SEQ ID NO 17
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 17
ccctgtttct tccacagtgc cta                                           23

<210> SEQ ID NO 18
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 18
```

```
gagacaatgg tctggttgcc atc                                            23

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
cctgcggctt aatttgactc                                                20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
aaccagacaa atcgctccac                                                20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
tacaacctga ccatcgcttg                                                20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
gcccccagag acttgttgta                                                20
```

RECOMBINANT HERPES SIMPLEX VIRUS FOR CANCER IMMUNOTHERAPY

This application is a U.S. National Stage Application of PCT/US2019/035922 filed Jun. 7, 2019 and claims benefit of priority to U.S. Provisional Patent Application Ser. No. 62/682,202, filed Jun. 8, 2018, the contents of each of which are incorporated herein by reference in their entirety.

This invention as made with government support under grant no. AI112755 awarded by the National Institutes of Health. The government has certain rights in this invention.

BACKGROUND

Oncolytic herpes simplex virus 1 (HSV-1) is an attractive agent for cancer immunotherapy (Peters & Rabkin (2015) *Mol. Ther. Oncolytics* 2:15010; Chiocca & Rabkin (2014) *Cancer Immunol. Res.* 2:295-300). Upon infection, HSV-1 undergoes sequential gene expression, DNA replication, assembly and egress, resulting in tumor cell destruction. This is accompanied by release of danger signals and neo-antigens that activate adaptive antitumor immunity. A range of oncolytic HSV is under various stages of development (Peters & Rabkin (2015) *Mol. Ther. Oncolytics* 2:15010). The most clinically advanced agent is talimogene laherparepvec (T-VEC) approved by FDA for treating advanced melanoma (Andtbacka, et al. (2015) *J. Clin. Oncol.* 33:2780-88). Additional examples of oncolytic HSV are G207, 1716 and ΔG47 that have undergone or are in clinical trials (Markert, et al. (2000) *Gene Ther.* 7:867-74; Rampling, et al. (2000) *Gene Ther.* 357:525-6; Streby, et al. (2017) *Clin. Cancer Res.* 23:3566-74; Fukuhara, et al. (2016) *Cancer Sci.* 107:1373-79). Although differing in backbone design, these oncolytic HSV viruses have originally deleted the $\gamma_1 34.5$ gene that codes for a virulence factor.

HSV $\gamma_1 34.5$ contains a large amino-terminal domain (aa 1-146) and carboxyl-terminal domain. In infected cells, HSV-1 activates double-stranded RNA dependent kinase (PKR) that shuts off protein synthesis by phosphorylation of translation initiation factor 2α (eIF-2α). As such, the $\gamma_1 34.5$ protein redirects protein phosphatase 1 (PP1) to dephosphorylate eIF-2α. Notably, site-specific disruption of the $\gamma_1 34.5$-PP interaction abrogates viral virulence. HSV $\gamma_1 34.5$ is also reported to affect glycoprotein processing and viral spread. In addition, evidence suggests that the $\gamma_1 34.5$ protein bears additional functions. These include inhibition of autophagy, IFN induction by TANK binding kinase 1, and dendritic cell maturation by Toll-like receptors and acceleration of nuclear egress. Although the $\gamma_1 34.5$ protein shuttles between the nucleus and cytoplasm, its precise interplay with host cells remains obscure.

Several lines of evidence demonstrate that HSV-1 mutants with deletion of the $\gamma_1 34.5$ gene exert antitumor activity. This has been shown for tumors, including glioma, colon, ovarian, breast, liver, and melanoma in immune-deficient as well as in immune-competent pre-clinical models (Mineta, et al. (1995) *Nat. Med.* 1:938-43; Toda, et al. (1998) *Hum. Gene Ther.* 9:2177-85; Chambers, et al. (1995) *Proc. Natl. Acad. Sci. USA* 92:1411-15; Randazzo, et al. (1995) *Virology* 211:94-101; Thomas & Fraser (2003) *Mol. Ther.* 8:543-51; Coukos, et al. (2000) *Clin. Cancer Res.* 6:3342-53; Braidwood, et al. (2014) *J. Hepatocell. Carcinoma* 1:149-61; Wang, et al. (2016) *Gene Ther.* 23:135-43; WO 2017/013419 A1; US 2017/0319638 A1; U.S. Pat. No. 7,223,593). However, the therapeutic outcome varies widely. Although the underlying events are complex, the nature of virus-host interactions seems a determinant. It has been suggested that the activation of mitogen-activated protein kinase or RAS oncogene in tumor cells inhibits PKR and thereby permits viral replication. On the other hand, genetic or epigenetic suppression of stimulated-interferon-gene (STING) is reported to license the $\gamma_1 34.5$ null mutant for tumor destruction as it mediates type I IFN production. Accordingly, active PKR, STING or IFN production in the tumor cells is believed to mitigate efficacy of oncolytic HSV that lacks the $\gamma_1 34.5$ gene.

A major limitation in the use of attenuated, replication-competent viruses to directly destroy tumors continues to be the reduced growth in many cell types, including cancer cells. Despite an initial wave of oncolysis, host defenses limit the viral vectors to replicate successfully for a long enough period of time to eradicate the entire population of neoplastic cells. Further, oncolytic viral backbones with improved replication often dampen innate immune priming necessary for antitumor immunity. As such, the surviving cancer cells proliferate or re-establish their strangle-hold on the patient. Thus, what is needed are viral anti-tumor agents that lyse cancer cells and activate systemic antitumor responses effectively.

SUMMARY OF THE INVENTION

This invention provides a method for treating a subject with cancer by administering to the subject a therapeutically effective amount of a recombinant Herpes Simplex Virus-1 (HSV-1) that expresses only a C-terminal portion of $\gamma_1 34.5$ protein, e.g., a protein consisting of SEQ ID NO:2, with no wild-type or intact $\gamma_1 34.5$ protein expression thereby treating the subject's cancer. In some embodiments, the recombinant HSV-1 further includes a deletion of one or more non-essential genes or fragments thereof, e.g., UL2, UL3, UL4, UL9.5, UL10, UL11, ULI2, UL13, ULI4, UL20, UL21, UL23, UL24, UL39, UL40, UL41, UL43, UL43.5, UL44, UL45, UL46, UL47, UL50, UL51, UL53, UL55, Us1, Us1.5, Us2, Us3, Us4, Us5, Us7, Us8, Us8.5, Us9, Us10, Us11, Us12, and ICP0. In other embodiments, the recombinant HSV-1 further includes replacement of one or more non-essential genes with one or more genes expressing a therapeutic protein (e.g., interferon alpha (IFN-α), interleukin-2 (IL-2), and granulocyte-colony stimulating factor (G-CSF)), enzyme, antibody (e.g., anti-programmed cell death protein 1 antibody (anti-PD1), anti-checkpoints T-lymphocyte-associated protein 4 antibody (anti-CTLA4), anti-OX40 (anti-CD134) antibody, and anti-CD40 antibody) or nucleic acid for cancer therapy, wherein the non-essential genes are selected from UL2, UL3, UL4, UL9.5, UL10, UL11, ULI2, UL13, ULI4, UL20, UL21, UL23, UL24, UL39, UL40, UL41, UL43, UL43.5, UL44, UL45, UL46, UL47, UL50, UL51, UL53, UL55, Us1, Us1.5, Us2, Us3, Us4, Us5, Us7, Us8, Us8.5, Us9, Us10, Us11, Us12, and ICP0. In still further embodiments, the cancer is a solid tumor and is optionally a cancer selected from breast, lung, liver, skin (melanoma), brain, and colon cancer. In addition to the administration of the recombinant HSV-1, the method may further include the administration of an effective amount of a second therapeutic agent useful for the treatment of cancer.

DETAILED DESCRIPTION OF THE INVENTION

Figure 1:
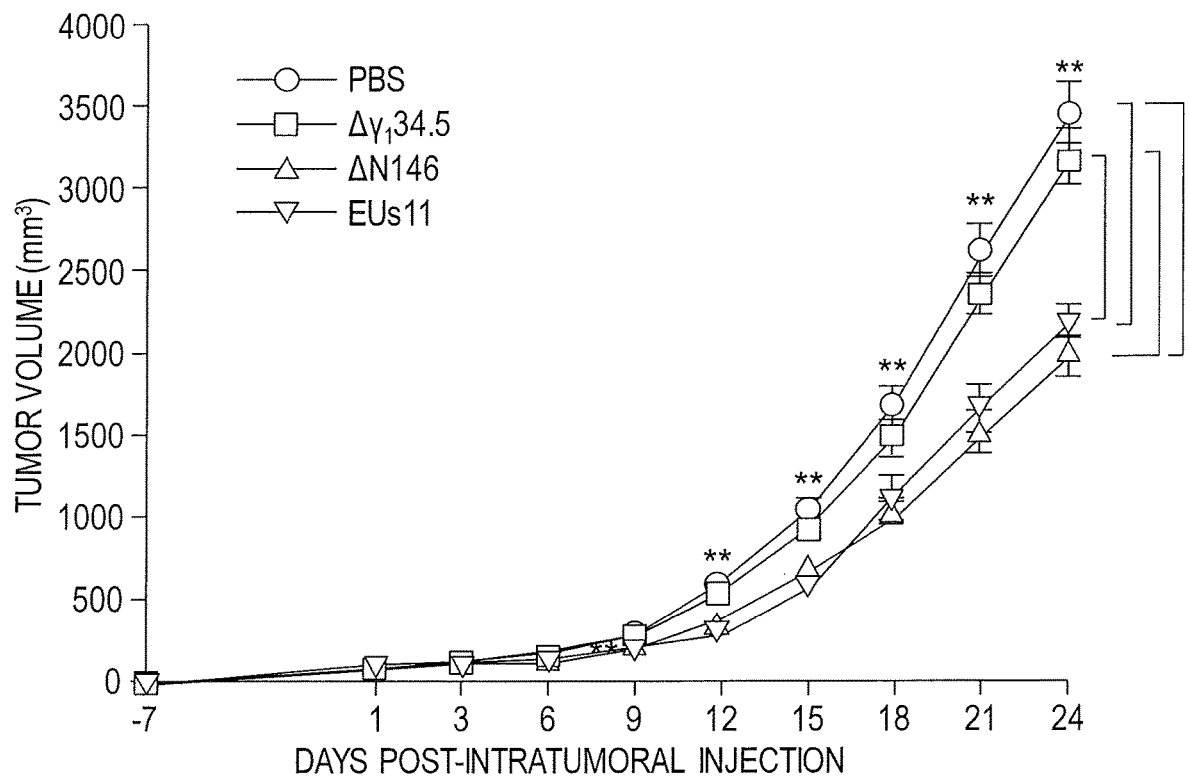
FIG. 1 provides data demonstrating that ΔN146 reduces local tumor growth. 4T1 cells were implanted subcutaneously into mice (day-7). Tumors formed were injected with PBS, Δγ₁34.5, ΔN146, or EUs11 suspended in PBS on days 1, 3, and 6. Tumor sizes were measured periodically (x axis) until day 24 (n=6 each group). Average tumor volumes over time are shown on the y axis. Asterisks indicate statistical significance by nonparametric analysis. The results shown are from one of three independent experiments. Differences between the selected groups were statistically assessed by a two-tailed Student t test (**, $P<0.01$).

The optimal intracellular environment for virus replication develops through events that begin to take place with attachment of virus to the cell membrane. Binding of the herpes simplex virus to the cell membrane receptor(s) is followed by a cascade of events that are associated with biochemical, physiological, and morphological changes in the cells. Following infection in susceptible cells, lytic replication is regulated by a temporally coordinated sequence of gene transcription. Binding of the virus to a host cell membrane activates the immediate-early (IE or α) genes (ICP0, ICP4, ICP22, ICP27, and ICP47), which are trans-activating factors allowing the production of the next group of genes to be transcribed, the early (β) genes. Expression of immediate-early gene products is followed by the expression of proteins encoded by the early and then, the late (γ) genes. The entire cascade of gene activation and viral replication in the wild-type virus takes about 18-24 hours and invariably results in cell death. The recombinant HSV mutant of the present invention circumvents the protein synthesis shutoff phenotype of γ₁34.5 null viruses and activates STING (interferon-stimulated genes) that mediate antitumor immunity, creating a more robust HSV variant with targeted γ₁34.5 deletion.

It has now been discovered that recombinant HSV-1, which expresses the C-terminal half of γ₁34.5 (ΔN146), robustly replicates in and lyses malignant cells that are refractory to the γ₁34.5 null mutant (Δγ₁34.5). In infected cells, ΔN146 but not Δγ₁34.5 precludes phosphorylation of translation initiation factor eIF2α, ensuing viral protein synthesis. Remarkably, ΔN146 also activates interferon regulatory factor 3 and the IFN response because it removes the γ₁34.5 inhibitory domain of STING, an immune factor known to prime immunity against tumor. However, unlike Δγ₁34.5, ΔN146 replicates competently when exposed to IFN-α/β. This is attributable to the activity associated with the C-terminal half of γ₁34.5. Although EUs11 replicates competently, it inactivates interferon regulatory IRF3. Thus, its replication comes at cost of immune inhibition. In a murine 4T1 tumor model, ΔN146 reduces tumor growth and metastasis more effectively than Δγ₁34.5. While comparable in tumor growth reduction, ΔN146 reduces metastasis more effectively than EUs11. This coincides with viral replication, IFN induction and T cell infiltration in local tumors. ΔN146 is undetectable in normal tissues and avirulent in vivo. Thus, selective editing of HSV-1 alters virus-cell interactions, which results in a unique anti-neoplastic platform, namely, tumor selectivity, immunostimulation and resistance to clearance by IFN. Accordingly, this invention is a recombinant HSV-1 virus that expresses only the C-terminal half of γ₁34.5 protein with no wild-type or intact γ₁34.5 protein expression and its use in the treatment of cancer.

As is known in the art, γ₁34.5 is an HSV protein that promotes viral replication in the peripheral tissues and penetration to the peripheral nervous systems in experimental models (Whitley, et al. (1993) *J. Clin. Invest.* 91:2837-43; Perng, et al. (1996) *J. Virol.* 70:2883-93; Mao & Rosenthal (2003) *J. Virol.* 77:3409-3417). In addition, it facilitates HSV infection and replication in the central nervous system (Chou, et al. (1990) *Science* 250:1262-66; MacLean, et al. (1991) *J. Gen. Virol.* 72:631-39). HSV γ₁34.5 is known to include a large amino-terminal domain (aa 1-146) and carboxyl-terminal domain (aa 147-263), which binds protein phosphatase 1α (He, et al. (1998) *J. Biol. Chem.* 273:20737-43). The nucleotide and amino acid sequence for wild-type γ₁34.5 are available under GENBANK Accession No. NC_001806.1, which provides the complete genome of HSV-1 strain 17; GENBANK Accession No. GU734771.1, which provides the complete genome of HSV-1 strain F; and GENBANK Accession No. GU734772.1, which provides the complete genome of HSV-1 strain H129. By way of illustration, a wild-type or intact γ₁34.5 has the amino acid sequence:

(SEQ ID NO: 1)
MARRRRHRGPRRPRPPGPTGAVPTAQSQVTSTPNSEPAVRSAPAAAPPPP

PASGPPPSCSLLLRQWLHVPESASDDDDDDWPDSPPPEPAPEARPTAAA

PRPRSPPPGAGPGGGANPSHPPSRPFRLPPRLALRLRVTAEHLARLRLRR

AGGEGAPEPPATPATPATPATPATPARVRFSPHVRVRHLVVWASAARLAR

RGSWARERADRARFRRRVAEAEAVIGPCLGPEARARALARGAGPANSV.

As used herein, "recombinant HSV-1" refers to an engineered or modified human herpes simplex virus 1 that expresses only the C-terminal portion or half of γ₁34.5 protein with no wild-type or intact γ₁34.5 protein expression. As used herein, the C-terminal portion or half of γ₁34.5 protein refers to the following amino acid residues of γ₁34.5 protein or its variants that retain or enhance antitumor activity:

(SEQ ID NO: 2)
RLRRAGGEGAPEPPATPATPATPATPATPARVRFSPHVRVRHLVVWASAA

RLARRGSWARERADRARFRRRVAEAEAVIGPCLGPEARARALARGAGPAN

SV.

In some aspects of the recombinant HSV-1 of this invention, the endogenous $\gamma_1 34.5$ gene has been modified such that both copies of the $\gamma_1 34.5$ gene only express the C-terminal portion of the $\gamma_1 34.5$ protein. In other aspects of the recombinant HSV-1 of this invention, both endogenous copies of the $\gamma_1 34.5$ gene have been deleted and nucleic acids encoding the C-terminal portion of the $\gamma_1 34.5$ protein have been inserted into one or more separate locations in the HSV-1 genome, e.g., in non-essential genes. In this respect, the HSV-1 genome has been modified so that the wild-type $\gamma 34.5$ gene is non-functional, but the recombinant HSV-1 can still infect, replicate within, and lyse tumor cells in a mammal.

Expression of C-terminal portion of the $\gamma_1 34.5$ protein can be driven by the $\gamma_1 34.5$ protein promoter, another endogenous HSV-1 promoter, or heterologous or exogenous promoter of viral or cellular origin. Exemplary promoters of use in the invention include, without limitation, the herpes simplex virus immediate-early promoters $\alpha 27$, $\alpha 4$, $\alpha 0$, $\alpha 22$, and $\alpha 47$; the herpes simplex virus early promoters from ICP8 (or $U_L 29$), thymidine kinase (tk or $U_L 23$), ICP6 ($U_L 39$) or any of the DNA replication genes; or late promoter, e.g., the Us11 promoter.

In some embodiments, the recombinant HSV-1 further includes the deletion of one or more non-essential genes of HSV-1. A non-essential gene is to be distinguished from an essential gene, in whose absence the virus will not replicate. A non-essential gene may be a beneficial gene, in which case the replacement of such beneficial gene will result in a virus that replicates at a much slower rate than that of the wild-type virus. Representative non-essential genes of HSV-1 include, but are not limited to, UL2, UL3, UL4, UL9.5, UL10, UL11, UL12, UL13, UL14, UL20, UL21, UL23, UL24, UL39, UL40, UL41, UL43, UL43.5, UL44, UL45, UL46, UL47, UL50, UL51, UL53, and UL55 in the UL region; Us1, Us1.5, Us2, Us3, Us4, Us5, Us7, Us8, Us8.5, Us9, Us10, Us11 and Us12 in the Us region; and ICP0 in the inverted repeat region.

In an alternative embodiment, one or more of non-essential genes has been replaced with one or more nucleic acids encoding and capable of expressing a therapeutic protein, enzyme, antibody, nucleic acid (e.g., a nucleic acid encoding said protein, enzyme, antibody, or a microRNA, ribozyme, and the like), or the like for cancer therapy. A therapeutic protein refers to a functional protein (i.e., other than that of an enzyme or antibody), which has a therapeutic benefit in the treatment of cancer. Examples of suitable therapeutic proteins include, but are not limited to, rsCD40L (Eliopoulos et al. (2000) Mol. Cell. Biol. 20:5503-5515); Fas-ligand (Sharma et al. (2000) Pharmacol. Ther. 88:333-347); TRAIL (Golstein (1997) Curr. Biol. 7: R750-753); TNF (Baker & Reddy (1996) Oncogene 12:1-9; Theys, et al. (1999) Appl. Environ. Microbiol. 65:4295-4300; Lammertyn, et al. (1997) Appl. Environ. Microbiol. 63:1808-1813); GM-CSF for the treatment of melanoma, breast carcinoma, colorectal carcinoma, glioblastoma, neuroblastoma, and prostate carcinoma (see, e.g., Eubank, et al. (2009) Cancer Res. 69(5):2133-40); IFN for the treatment of ovarian carcinoma and solid tumors (see, e.g., Goto, et al. (1996) Br. J. Cancer 74:546-54); IL-2 for the treatment of neuroblastoma and ovarian carcinoma (see, e.g., Minor, et al. (2017) Gynecol. Oncol. Rep. 22:43-44); and G-CSF for the treatment of breast carcinoma, bladder carcinoma, ovarian carcinoma (see, e.g., Omura, et al. (1996) Proc. Annu. Meet Am. Soc. Clin. Oncol. 15: A755).

A therapeutic enzyme refers to an enzyme, which has a therapeutic benefit in the treatment of cancer. Therapeutic enzymes of particular use include enzymes capable of converting a nontoxic prodrug into a toxic drug which is cytotoxic to a tumor. Examples of suitable therapeutic enzyme-prodrug pairs include, but are not limited to, Herpes simplex virus thymidine kinase (HSV-TK)+Ganciclovir (GCV)(Moolten (1986) Cancer Res. 46:5276-5281); HSV-TK A-5021 (1'S,2'R)–9{[1',2'-bis(hydroxymethyl) cycloprop-1'-yl]methyl} guanine (Hasegawa, et al. (2000) Cancer Gene Ther. 7:557-562); Horseradish peroxidase (HRP)+ Indole-3-acetic acid (IAA)(Greco, et al. (2000) Cancer Gene Ther. 7:1414-1420); bacterial enzyme carboxypeptidase G2 (CPG2)+4-([2-chloroethyl] [2-mesyloxyethyl]amino)benzoyl-L-glutamic acid (CMDA) or +4-[N,N-bis(2-iodoethyl) amino]phenoxycarbonyl L-glutamic acid (ZD2767P) (Spooner, et al. (2000) Cancer Gene Ther. 7:1348-1356; Webley, et al. (2001) Br. J. Cancer 84:1671-1676); Human cytochrome P450 CYPIA2+acetaminophen (Thatcher, et al. (2000) Cancer Gene Ther. 7:521-525); Rabbit cytochrome P450 4B1 (CYP4B1)+4-ipomeanol (4-IM) (Mohr, et al. (2000) Cancer Gene Ther. 7:1008-1014; Heuser, et al. (2000) Cancer Gene Ther. 7:806-12); Rat cytochrome P450 4B1 (CYP2B1)+oxaphosporines, such as ifosfamide (IFO) (Kammertoens, et al. (2000) Cancer Gene Ther. 7:629-636); E. coli nitroreductase (NTR)+CB1954 (Djeha, et al. (2000) Cancer Gene Ther. 7: 721-731; Djeha, et al. (2001) Mol. Ther. 3:233-240); E. coli cytosine deaminase (CD), E. coli uracil phosphoribosyltransferase (UPRT)+5-fluorocytosine (5-FC)(Kammertoens, et al. (2000) Cancer Gene Ther. 7:629-636; Block, et al. (2000) Cancer Gene Ther. 7:438-445; Bentires-Alj, et al. (2000) Cancer Gene Ther. 7:20-6); Cytochrome P450 enzymes+cyclophosphamide (CPA) (Huang, et al. (2000) Cancer Gene Ther. 7:1034-42; Kan, et al. (2001) Cancer Gene Ther. 8:473-82); rabbit carboxylesterase+7-ethyl-10-[4-(1-piperidino)-1-piperidino] carbonyloxycamptothecin (CPT-II) (Meck, et al. (2001) Cancer Res. 61:5083-89); Mushroom tyrosinase+bis-(2-chloroethyl)amino-4-hydroxyphenylaminomethanone 28 (Jordan, et al. (2001) Bioorg. Med. Chem. 9:1549-58); E. coli β-galactosidase+1-chloromethyl-5-hydroxy-1,2-dihydro-3H-benz[e]indole (CC-1065) or +1-(1'-chloroethyl)-5-hydroxy-1,2-dihydro-3H-benz[e]indole (Tietze, et al. (2001) Chembiochem. 2:758-765); a mutant of carboxypeptidase G2 (CPG2, glutamate carboxypeptidase+4-[bis(2-iodoethyl) amino] phenyloxycarbonyl-L-glutamic acid or +3-fluoro-4-[bis(2-chlorethyl)amino]benzoyl-L-glutamic acid or +3,5-difluoro-4-[bis(2-iodoethyl)amino]benzoyl-L-glutamic acid (Friedlos, et al. (2002) Cancer Res. 62:1724-1729).

A therapeutic antibody refers to an antibody that which has a therapeutic benefit in the treatment of cancer. Examples of suitable therapeutic antibodies include, but are not limited to, Atezolizumab (for the treatment of bladder cancer and breast cancer, NSCLC, and small cell lung cancer (SCLC)); Avelumab (for the treatment of bladder cancer and Merkel cell carcinoma (MCC)); Durvalumab (for the treatment of bladder cancer and NSCLC); Nivolumab (for the treatment of bladder cancer, colorectal cancer, kidney cancer, liver cancer, NSCLC, metastatic SCLC, Hodgkin lymphoma, and melanoma); Pembrolizumab (for the treatment of bladder cancer, cervical cancer, colorectal cancer, esophageal cancer, liver cancer, NSCLC, Hodgkin lymphoma, melanoma, and MCC); Bevacizumab (for the treatment of glioblastoma, cervical cancer, colorectal cancer, kidney cancer, non-small cell lung cancer (NSCLC), and ovarian cancer); Dinutuximab (for the treatment of neuroblastoma); Pertuzumab (for the treatment of breast cancer); Trastuzumab (for the treatment of breast cancer and esophageal cancer); Cetuximab (for the treatment of colorectal cancer); Panitumumab (for the treatment of colorectal cancer); Ramucirumab (for the treatment of colorectal cancer and esophageal cancer); Alemtuzumab (for the treatment of chronic lymphocytic leukemia (CLL)); Blinatumomab (for the treatment of acute lymphoblastic leukemia (ALL)); Obinutuzumab (for the treatment of CLL and non-Hodgkin lymphoma); Ofatumumab (for the treatment of CLL); Rituximab (for the treatment of CLL and non-Hodgkin Lymphoma); Necitumumab (for the treatment of NSCLC); Ipilimumab (for the treatment of melanoma, pancreatic cancer, prostate carcinoma and melanoma); Daratumumab (for the treatment of multiple myeloma); Elotuzumab (for the treatment of multiple myeloma); Denosumab (for the treatment of bone cancer); Olaratumumab (for the treatment of bone cancer); Cemiplimab (for the treatment of Merkel cell carcinoma (MCC)); MEDI0562; GSK3174998; PF-04518600; CP-870,893; dacetuzumumab; ADC-1013; and Ramucirumab (for the treatment of stomach or gastroesophageal cancer).

Methods of preparing a recombinant virus are known in the art. Briefly, to construct recombinant HSV, a gene of interest is cloned into a transfer plasmid. This plasmid is then co-transfected with HSV-1 genomic DNA (with a target gene replaced with HSV thymidine kinase gene) into rabbit skin cells. The progeny of the recombinant virus are selected and plaque-purified on 143 TK mutant cells in medium including of mixture 199V supplement with 100 μg of bromodeoxyuridine/ml and 2% fetal calf serum. Next, the thymidine kinase gene is restored by co-transfection of progeny viral DNA and a plasmid encoding the thymidine kinase gene in HAT medium. Preparation of viral stocks and titrations of infectivity are done with Vero cells.

As demonstrated herein, a recombinant HSV-1, which expresses only the C-terminal half of $\gamma_1 34.5$ protein with no wild-type or intact $\gamma_1 34.5$ protein expression, elicits immune activation, and robustly replicates in and lyses malignant cells that are refractory to the $\gamma_1 34.5$ null mutant ($\Delta\gamma_1 34.5$). Accordingly, this invention provides a method for treating a subject with cancer by administering to the subject, e.g., a human, a therapeutically effective amount of a recombinant HSV-1 that expresses only a C-terminal portion of $\gamma_1 34.5$ protein (in particular SEQ ID NO:2) with no wild-type or intact $\gamma_1 34.5$ protein expression thereby treating the subject's cancer. The recombinant HSV-1 can be administered as the sole anticancer therapy, or in conjunction with a therapeutically effective amount of a second anticancer agent, such as radiation and/or chemotherapy. Moreover, the method can also include the use of a target-specific moiety (e.g., antibody or cell marker) suitable for targeted administration of the recombinant HSV-1 of the present invention to the desired tissue.

As used herein, the terms "treat," "treating," "treatment," and the like refer to eliminating, reducing, relieving, reversing, and/or ameliorating a disease or condition and/or symptoms associated therewith, in this case treating cancer. Solid and non-solid tumors that can be treated in accordance with the method herein, include cancers of the bladder, breast, colon, kidney, liver, lung, ovary, pancreas, stomach, cervix, including squamous cell carcinoma; carcinoma, including thyroid and carcinomas of the skin; leukemia, including acute lymphocytic leukemia, acute lymphoblastic leukemia, acute and chronic myelogenous leukemia and promyelocytic leukemia; lymphoma including B cell lymphoma, T cell lymphoma, and Burkitt lymphoma; fibrosarcoma and rhabdomyosarcoma; melanoma; and neuroblastoma, astrocytoma and glioma. In certain embodiments, the cancer being treated in accordance with the method herein is a solid tumor. In other embodiments, the cancer is selected from breast, liver, lung, skin (melanoma), brain, and colon cancer.

Although not precluded, treating a disease or condition does not require that the disease, condition, or symptoms associated therewith be completely eliminated, including the treatment of acute or chronic signs, symptoms and/or malfunctions. "Treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. "Treatment" therefore also includes relapse prophylaxis or phase prophylaxis. The term "treat" and synonyms contemplate administering a therapeutically effective amount of the recombinant HSV-1 of the invention to an individual in need of such treatment. A treatment can be orientated symptomatically, for example, to suppress symptoms. Treatment can be carried out over a short period, be oriented over a medium term, or can be a long-term treatment, for example within the context of a maintenance therapy.

The term "therapeutically effective amount" or "effective dose" as used herein refers to an amount of the active ingredient(s) that, when administered, is (are) sufficient, to efficaciously deliver the active ingredient(s) for the treatment of a condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; and/or relieve, to some extent, one or more of the symptoms associated with the cancer. To the extent the administered active ingredient(s) prevents growth and/or kills existing cancer cells, it may be cytostatic and/or cytotoxic.

The recombinant HSV-1 of the invention can be used as is, provided via live carrier cells, or formulated in a pharmaceutical composition containing a pharmaceutically acceptable excipient. Pharmaceutical compositions provided herein can be specially formulated for intravenous administration in solid or liquid form or for intravenous injection. Optimal pharmaceutical compositions can be determined by one skilled in the art depending upon, for example, the intended route of administration, delivery format and desired dosage. See, for example, Remington's Pharmaceutical Sciences (19$^{th}$ edition, 1995).

The recombinant HSV-1 can be incorporated in a conventional systemic dosage form, such as an injectable formulation. The dosage form may also include the necessary physiologically acceptable carrier material, excipient, lubricant, buffer, surfactant, antibacterial, bulking agent (such as mannitol), antioxidants (ascorbic acid or sodium bisulfite) or the like.

The primary carrier or excipient in a pharmaceutical composition may be either aqueous or nonaqueous in nature.

For example, a suitable carrier or excipient may be water for injection, physiological saline solution or artificial cerebrospinal fluid, possibly supplemented with other materials common in compositions for parenteral administration. Neutral-buffered saline or saline mixed with serum albumin are further exemplary vehicles. Pharmaceutical compositions can include Tris buffer of about pH 7.0-8.5, or acetate buffer of about pH 4.0-5.5, which may further include sorbitol or a suitable substitute therefor. Pharmaceutical compositions of the invention may be prepared for storage by mixing the selected composition having the desired degree of purity with optional formulation agents (Remington's Pharmaceutical Sciences, Id.) in the form of a lyophilized cake or an aqueous solution. Further, the recombinant HSV-1 may be formulated as a lyophilizate using appropriate excipients such as sucrose.

Administration routes for the recombinant HSV-1, or pharmaceutical compositions of the invention include injection by intravenous, intraperitoneal, intracerebral (intraparenchymal), intracerebroventricular, intramuscular, intraocular, intraarterial, intraportal, or intralesional routes; by sustained release systems or by implantation devices. Compositions may be administered by bolus injection or continuously by infusion, or by implantation device. Compositions also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

The compositions of the invention can be delivered parenterally. When parenteral administration is contemplated, the therapeutic compositions for use in this invention may be in the form of a pyrogen-free, parenterally acceptable aqueous solution including the desired active ingredient(s) in a pharmaceutically acceptable vehicle. A particularly suitable vehicle for parenteral injection is sterile distilled water in which the active ingredient(s) is formulated as a sterile, isotonic solution, appropriately preserved. Preparation can involve the formulation of the desired active ingredient(s) with an agent, such as injectable microspheres, bio-erodible particles, polymeric compounds (such as polylactic acid or polyglycolic acid), beads or liposomes, that may provide controlled or sustained release of the active ingredient(s), which may then be delivered via a, depot injection. Formulation with hyaluronic acid has the effect of promoting sustained duration in the circulation. Implantable drug delivery devices may be used to introduce the desired active ingredient(s).

This invention also includes methods for treating cancer by administering to an individual in need thereof the recombinant HSV-1 of the invention and one or more second therapeutic agents useful for the treatment of cancer. The recombinant HSV-1 and the second therapeutic agent can be administered simultaneously or sequentially. In addition, the recombinant HSV-1 and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

In some embodiments, the second therapeutic agent is an antibody. Suitable antibodies include, but are not limited to, Atezolizumab; Avelumab; Durvalumab; Nivolumab (anti-PD1); Pembrolizumab (anti-PD1); Bevacizumab; Dinutuximab; Pertuzumab; Trastuzumab; Cetuximab; Panitumumab; Ramucirumab; Alemtuzumab; Blinatumomab; Obinutuzumab; Ofatumumab; Rituximab; Necitumumab; Ipilimumab (anti-CTLA4); Daratumumab; Elotuzumab; Denosumab; Olaratumumab; Cemiplimab; MEDI0562 (anti-OX40), GSK3174998 (anti-OX40), PF-04518600 (anti-OX40), CP-870,893 (anti-CD40), dacetuzumumab (anti-CD40), ADC-1013 (anti-CD40), and Ramucirumab.

In other embodiments, the second therapeutic agent includes is a chemotherapeutic agent, radiotherapeutic agent, anti-angiogenic agent, apoptosis-inducing agent, anti-tubulin drug or a tumor-targeted chemotherapeutic agent, radiotherapeutic agent, anti-angiogenic agent, apoptosis-inducing agent or anti-tubulin drug. Exemplary second therapeutic agents include, but are not limited to, anti-angiogenic agents such as angiostatin, endostatin, vasculostatin, canstatin and maspin and anti-tubulin drugs such as colchicine, taxol, vinblastine, vincristine, vindescine, a combretastatin or a derivative or prodrug thereof. Other examples of second therapeutic agents include, but are not limited to, alkylating agents, nitrogen mustards, cyclophosphamide, trofosfamide, chlorambucil, nitrosoureas, carmustine (BCNU), lomustine (CCNU), alkylsulphonates, busulfan, treosulfan, triazenes, plant alkaloids, vinca alkaloids (vineristine, vinblastine, vindesine, vinorelbine), taxoids, DNA topoisomerase inhibitors, epipodophyllins, 9-aminocamptothecin, camptothecin, crisnatol, mitomycins, mitomycin C, anti-metabolites, anti-folates, DHFR inhibitors, trimetrexate, IMP dehydrogenase inhibitors, mycophenolic acid, tiazofurin, ribavirin, EICAR, ribonuclotide reductase inhibitors, hydroxyurea, deferoxamine, pyrimidine analogs, uracil analogs, floxuridine, doxifluridine, ratitrexed, cytosine analogs, cytarabine (ara C), cytosine arabinoside, fludarabine, purine analogs, mercaptopurine, thioguanine, DNA antimetabolites, 3-HP, 2'-deoxy-5-fluorouridine, 5-HP, alpha-TGDR, aphidicolin glycinate, ara-C, 5-aza-2'deoxycytidine, beta-TGDR, cyclocytidine, guanazole (inosine glycodialdehyde), macebecin II, pyrazoloimidazole, hormonal therapies, receptor antagonists, anti-estrogen, tamoxifen, raloxifene, megestrol, LHRH agonists, goserelin, leuprolide acetate, anti-androgens, flutamide, bicalutamide, retinoids/deltoids, cis-retinoic acid, vitamin A derivatives, all-trans retinoic acid (ATRA-IV), vitamin D3 analogs, CB1093, ICH1060, photodynamic therapies, vertoporfin, BPD-MA, phthalocyanine, photosensitizer Pc4, demethoxy-hypocrellin A (2BA-2-DMHA), cytokines, interferon-α, interferon-β, interferon-γ, tumor necrosis factor, angiogenesis inhibitors, angiostatin (plasminogen fragment), antiangiogenic antithrombin UI, angiozyme, ABT-627, Bay 12-9566, benefin, BMS-275291, cartilage-derived inhibitor (CDI), CD59 complement fragment, CEP-7055, Col 3, combretastatin A-4, endostatin (collagen XVIII fragment), fibronectin fragment, Gro-beta, halofuginone, heparinases, heparin hexasaccharide fragment, HMV833, human chorionic gonadotropin (hCG), IM-862, interferon inducible protein, interleukin-12, kringle 5 (plasminogen fragment), marimastat, metalloproteinase inhibitors (UMPs), 2-methoxyestradiol, MMI270 (CGS 27023A), neovastat, NM-3, panzem, PI-88, placental ribonuclease inhibitor, plasminogen activator inhibitor, platelet factor-4 (PF4), prinomastat, prolactin 161, proliferin related protein (PRP), retinoids, solimastat, squalamine, SS3304, SU5416, SU6668, SU11248, tetrahydrocortisol-S, tetrathiomolybdate, thalidomide, thrombospondin-1 (TSP-1), TNP-470, transforming growth factor-beta, vasculostatin, vasostatin (calreticulin fragment), ZD6126, ZD6474, farnesyl transferase inhibitors (FTI), bisphosphonates, antimitotic agents, allocolchicine, halichondrin B, colchicine, colchicine derivative, dolstatin 10, maytansine, rhizoxin, thiocolchicine, trityl cysteine, isoprenylation inhibitors, dopaminergic neurotoxins, cell cycle inhibitors, staurosporine, actinomycins, actinomycin D, dactinomycin, bleomycins, bleomycin A2, bleomycin B2, peplomycin, anthracycline, adriamycin, epirubicin, pirarnbicin, zorubicin, mitoxantrone, MDR inhibitors, verapamil, Ca21A TPase inhibitors, and thapsigargin.

The following non-limiting examples are provided to further illustrate the present invention.

Example 1

Materials and Methods

*Cells and Viruses.* Vero, HT-29, SW480, C32, A375, MDA-MB-231, 4T1, HepG2 and A549 cells were obtained from the American Type Culture Collection. Vero, SW480, C32, A375, MDA-MB-231 and A549 cells were propagated in Dulbecco's modified Eagle's medium (DMEM) supplemented with 10% fetal bovine serum. HT-29, 4T1 and HepG2 cells were propagated in RPMI1640 supplemented with 10% fetal bovine serum. HSV-1(F) is a prototype HSV-1 strain used in this study (Ejercito, et al. (1968) *J. Gen. Virol.* 2:357-364). In recombinant virus $\Delta\gamma_1 34.5$, a 1-kb fragment from the coding region of the $\gamma_1 34.5$ gene was deleted (Chou, et al. (1990) *Science* 250:1262-1266). In $\Delta$N146, the sequences of $\gamma_1 34.5$ gene encoding amino acids 1 to 146 were deleted (Ma, et al. (2012) *J. Virol.* 86:2188-2196). In EUs11, the $\gamma_1 34.5$ gene was deleted but with the Us11 gene driven by the $\alpha$-47 promoter (Liu, et al. (2018) *J. Virol.* 92). Preparation of viral stock and titration of infectivity were carried out as described previously (Ma, et al. (2012) *J. Virol.* 86:2188-2196).

Viral Infections. Viral infections were carried out at indicated multiplicities of infection (Verpooten, et al. (2009) *J. Biol. Chem.* 284:1097-1105). Cells were then harvested and processed for immunoblot, real-time PCR analysis or viral growth analysis (Ma, et al. (2012) *J. Virol.* 86:2188-96; Wu, et al. (2016) *J. Virol.* 90:10414-22). The cell viability was determined by CELLTITER-GLO® Luminescent Cell Viability Assay (Promega) according to the manufacture protocols. For the interferon assay, Vero and MDA-MB-231 cells were untreated or treated with human interferon-$\alpha$ (Sigma), and 4T1 cells were treated with mouse interferon-$\alpha$ (Sigma) for 20 hours. Cells were then infected with viruses and viral yields were determined at 48 hours post-infection.

Immunoblot Analysis and ELISA. Cells were harvested, washed with phosphate-buffered saline (PBS), and lysed with ice-cold buffer (50 mM Tris-HCl pH 7.4, 150 mM NaCl, 5 mM EDTA, 1.0% Triton™ X-100, and protease inhibitor cocktail) on ice. After centrifugation, supernatants were mixed with disruption buffer (50 mM Tris-HCl pH 6.8, 2% (wt/vol) SDS, 0.1% bromophenol blue, 10% glycerol, and 100 nM ($\beta$-mercaptoethanol) and boiled. Samples were then subjected to electrophoresis on denaturing polyacrylamide gels, transferred to nitrocellulose membranes, and reacted with antibodies against gC (Jing, et al. (2004) *J. Virol.* 78:7653-66), $\gamma_1 34.5$ (Cheng, et al. (2002) *J. Virol.* 76:9434-45), ICP27 (Virusys Inc.), ICP0 (Santa Cruz), eIF-2$\alpha$ (Cell Signaling Technology, Inc.), phosphorylated eIF-2$\alpha$ (Cell Signaling Technology, Inc.), IRF3 (Cell Signaling Technology, Inc.), phosphorylated IRF3 (Cell Signaling Technology, Inc.) and $\beta$-actin (Sigma). The membranes were rinsed in PBS and reacted with either donkey anti-rabbit or anti-mouse immunoglobulin conjugated to horseradish peroxidase and developed with an enhanced chemiluminescence western blot detection system kit (Amersham Pharmacia Biotechnology, Inc.). To perform enzyme-linked immunosorbent assays (ELISA), supernatants of cell culture were collected to analyze IFN-$\alpha$ and Cxc19 according to the manufacturer's instructions (R&D Systems).

Transcriptome Analysis. Monolayers of 4T1 cells were mock-infected or infected with viruses (5 pfu/cell). At 6 hours post-infection, RNA was extracted from the cells using the RNase plus mini kit (Qiagen) and treated with DNase I (New England BioLabs). Duplicate RNA samples were processed using Clariom™ S Affymetrix array by Center for Genomic Research at University of Illinois at Chicago. Raw data generated from Clariom™ S Mouse Array was processed in R using package Oligo. Feature intensity values from each CEL file was converted into normalized expression value using Robust Multi-array Average (RMA) with default settings. All the positive and negative control probes, along with Affymetrix report genes (RPTR) were removed before performing the downstream analysis. PCA (Principle Component Analysis) plots were generated to check for any batch-effect. Differential gene expression analysis was performed using limma package. Significantly expressed genes were filtered for adjusted-p value of <0.05. Heat maps were produced from the primary data (the normalized expression value) using the R package "pheatmap" v1.0.8.

Quantitative Real-Time PCR Assay. Cells were mock-infected or infected with viruses. At 6 hours after infection, total RNA was harvested from cells using an RNase plus mini kit (Qiagen) and subjected to DNase I digestion (New England BioLabs). cDNA was synthesized using a high capacity cDNA reverse transcription kit (Applied Biosystems). Quantitative real-time PCR was performed using an Applied Biosystems ABI Prism 7900HT instrument with ABI SYBR® green master mix (Applied Biosystems). Gene expression levels were normalized to endogenous control 18S rRNA. Relative gene expression was determined by the $2^{-\Delta\Delta CT}$ method (Schmittgen & Livak (2008) Nat. Protoc. 3:1101-8). Primers for each gene were chosen according to the recommendation of the qPrimerDepot database. Primer sequences are provided in Table 1.

TABLE 1

| Gene | | Primer Sequence | SEQ ID NO: |
|---|---|---|---|
| Mouse IFN-α1 | Forward | GCCTTGACACTCCTGGTACAAATGAG | 3 |
| | Reverse | CAGCACATTGGCAGAGGAAGACAG | 4 |
| Mouse IFIT1 | Forward | CAAGGCAGGTTTCTGAGGAG | 5 |
| | Reverse | AAGCAGATTCTCCATGACCTG | 6 |
| Mouse Ccl5 | Forward | CTGCTGCTTTGCCTACCTCT | 7 |
| | Reverse | CACTTCTTCTCTGGGTTGGC | 8 |
| Mouse Cxcl9 | Forward | TCCTTCCTTCCTTCCTTCCTTCC | 9 |
| | Reverse | AGGCTCTTTTTCACCCTGTCTGG | 10 |
| Human IFN-α1 | Forward | GGCCTTGACCTTTGCTTTACTG | 11 |
| | Reverse | CACAGAGCAGCTTGACTTGCA | 12 |
| Human IFITI | Forward | CCTCCTTGGGTTCGTCTACA | 13 |
| | Reverse | AGTGGCTGATATCTGGGTGC | 14 |

TABLE 1-continued

| Gene | | Primer Sequence | SEQ ID NO: |
|---|---|---|---|
| Human Ccl5 | Forward | CCTGCTGCTTTGCCTACATT | 15 |
| | Reverse | ACACACTTGGCGGTTCTTTC | 16 |
| Human Cxcl9 | Forward | CCCTGTTTCTTCCACAGTGCCTA | 17 |
| | Reverse | GAGACAATGGTCTGGTTGCCATC | 18 |
| 18s rRNA | Forward | CCTGCGGCTTAATTTGACTC | 19 |
| | Reverse | AACCAGACAAATCGCTCCAC | 20 |

Mice Studies. Five-week-old mice BALB/c mice were purchased from Harlan Sprague Dawley Inc. and housed under specific-pathogen-free conditions in a biosafety level 2 containment. All experimental procedures involving animals were approved by the institutional animal care and use committee of University of Illinois at Chicago. At 6 weeks of age, 1×10⁵ viable 4T1 cells suspended in 0.1 ml of PBS were inoculated subcutaneously into the right flank of mice (day −7). When the tumor reached a volume of approximately 100 mm³ eight days after, mice were randomly assigned into three groups for intra-tumor injections of Δγ₁34.5, ΔN146 or PBS on days 1, 3 and 6. Each tumor was injected slowly with a total of 1×10⁷ PFU of virus or PBS in a volume of 0.1 ml. The tumor growth was monitored every other day by measuring two perpendicular tumor diameters with a digital caliper. Tumor volumes were calculated using the following formula: volume=(length×width×height)/2. On day 24 after tumor inoculation, mice were euthanized by CO₂ inhalation.

Tissue Analysis. On selected days after the last intratumor injection, six mice from each treatment group were sacrificed to collect the tumor, lung, liver, spleen and blood. To measure viral load, the samples were minced, homogenized and bead-beaten, freeze-thawed three times, and sonicated in DMEM. After centrifugation, the tumor supernatants were used for plaque assays. The supernatants from the lung, liver, spleen and blood were used for quantitative real-time PCR assay. Briefly, the supernatants were suspended in buffer containing 1% SDS, 50 mM Tris (pH 7.5), and 10 mM EDTA. After incubation with proteinase K (50 µg/ml) at 37° C., viral DNA was extracted and quantified by real-time PCR using HSV-1 gD-specific primers:

TACAACCTGACCATCGCTTG    (SEQ ID NO: 21)
and

GCCCCCAGAGACTTGTTGTA.    (SEQ ID NO: 22)

For metastatic formation assays, lungs from mice were excised, and fixed in formalin. The number of lung metastases was quantified by counting under a light microscope.

Immunohistochemistry Analysis. Tissue sections were processed and HSV-1 antigens were detected with antibody against HSV-1 (Dako). CD4 (Cell Signaling Technology, Inc.) and CD8 (Cell Signaling Technology, Inc.) antibodies were used according to the manufacture protocol. Samples were incubated with primary antibody prior to the addition of biotinylated anti-rabbit immunoglobulin secondary antibody, avidin-horseradish peroxidase, and 3,3'-diaminobenzidine tetrahydrochloride (0.04%) in 0.05 M Tris-HCl (pH 7.4) and 0.025% H₂O₂ as a chromogen (Ventana Medical Systems, Tucson, AZ).

Example 2

ΔN146 Mutant Replicates in Tumor Cells

It has been shown that an HSV γ₁34.5 mutant (ΔN146), with only amino acids 147-263, is substantially impaired for viral growth in normal cells or tissues (Ma, et al. (2012) *J. Virol.* 86:2188-2196; Ma, et al (2017) *Sci. Rep.* 7:41461; Pan, et al (2018) *J. Virol.* 92: e01015-18). To determine activity of this mutant in malignant cells, viral replication as assessed. This analysis indicated that in 4T1 (murine breast carcinoma) cells, wild-+type HSV-1 replicated to 1×10⁷ pfu/ml whereas the γ₁34.5 null mutant (Δγ₁34.5) reached only 1×10³ pfu/ml. However, ΔN146 grew to 1×10⁶ pfu/ml, indicative of robust replication. A similar trend was observed in MDA-MB-231 (human breast adenocarcinoma) cells where ΔN146 replicated 100-fold better than Δγ₁34.5. Moreover, these phenotypes were recapitulated in a range of other tumor cells including human HT29 (colon), SW480 (colon), HepG2 (liver), C32 (melanoma), A375 (melanoma) and A549 (lung).

Subsequently, the kinetics of viral growth were examined. HSV-1 grew steadily in 4T1 cells wild-type as infection progressed, with a titer increasing to 1×10⁷ pfu/ml by 72 hours post infection. ΔN146 replicated to 1×10⁶ pfu though at a slightly lower level and Δγ₁34.5 barely replicated, with a titer of 1×10³ pfu/ml throughout infection. A similar trend was observed in MDA-MB-231 cells where ΔN146 replicated 100-fold better than Δγ₁34.5. To assess viral cytolytic activity, cell viability was measured. This analysis indicated that similar to wild-type virus, ΔN146 lysed almost 95% of 4T1 cells by 72 hours, with a slightly delayed kinetics, whereas Δγ₁34.5 destroyed approximately 40% cells. Such effects were also mirrored in MDA-MB-231 cells. Together, these results indicate that ΔN146 replicates in and lyses tumor cells more effectively than the γ₁34.5 null mutant.

Example 3

Expression of the C-terminal Portion of γ₁34.5 Inhibits eIF2α Phosphorylation

HSV infection proceeds in a temporal manner, with sequential expression of α, β, and γ genes. Onset of viral DNA replication invokes the cessation of protein synthesis in the absence of γ₁34.5 (Chou & Roizman (1992) *Proc. Natl. Acad. Sci. USA* 89:3266-70). To assess the impact of ΔN146, expression of representative proteins ICP27 (α protein) and gC (γ protein) was measured as the expression of these proteins relies on viral DNA replication. Cells were mock-infected or infected with HSV-1, Δγ₁34.5 or ΔN146 virus and at 12 hours post-infection, samples were subjected to western blot analysis. This analysis indicated that wild-type virus expressed both ICP27 and gC in infected 4T1 and MDA-MB-231 cells. Although Δγ₁34.5 expressed ICP27, little gC was detectable in either of the 4T1 or MDA-MB-231 cells. Under these same conditions, ΔN146 expressed a comparable level of ICP27 and gC as wild-type HSV-1, indicating its ability to block translational arrest initiated by viral DNA replication.

As phosphorylation of eIF2α is coupled to protein synthesis, phosphorylation of eIF2α by stress kinases PKR, PERK or GCN2 was monitored in 4T1 and MDA-MB-231 tumor cells. This analysis indicated that expression of eIF2α was comparable in mock- or virus-infected tumor cells. Interestingly, phosphorylated eIF2α was present in mock-infected cells, likely due to oncogenic stress. Although wild-type HSV-1 eliminated eIF2α phosphorylation Δγ₁34.5 aggravated it and ΔN146 completely abrogated eIF2α phosphorylation in 4T1 and MDA-MB-231 tumor cells. Accordingly, the region spanning the C-terminal portion of γ₁34.5 is sufficient to inhibit eIF2α phosphorylation in tumor cells.

Example 4

ΔN146 Stimulates Interferon Responses in Tumor Cells

To assess tumor cell responses to viral infection, transcriptome analysis in 4T1 cells was carried out. It was observed that numerous genes in diverse cellular pathways were expressed differentially in 4T1 cells mock infected and infected with viruses. Of note, many genes in the innate immune pathways were evidently up-regulated in response to ΔN146. Among the 46 genes tested, most remained unchanged or marginally expressed in cells mock infected or infected wild-type virus. However, they were upregulated in cells infected with Δγ₁34.5, albeit to a different extent. Notably, gene induction was more pronounced in cells infected with ΔN146, indicating that ΔN146 has a propensity to stimulate the inflammatory response.

To confirm these results, the expression of selected cytokines and interferon-stimulated genes was determined by real-time PCR. As expected, wild-type virus triggered little expression of IFN-α1, IFIT1, Ccl5, and Cxcl9 whereas Δγ₁34.5 or ΔN146 sharply induced these genes. This was corroborated by the levels of cytokine production in ELISA assay. To dissect the molecular basis, interferon regulatory factor (IRF3), which activates immune responses, was analyzed. IRF3 was un-phosphorylated in 4T1 cells mock infected or infected with wild-type HSV-1. In contrast, it became phosphorylated in cells infected with Δγ₁34.5 or ΔN146. This was not due to differences in viral infectivity as indicated by the normal expression of ICP0 and ICP27. These results were confirmed in multiple experiments and phenotypes were seen in human MDA-MB-231 cells as well. It was concluded that like Δγ₁34.5, ΔN146 is immune-stimulatory upon infection of malignant cells.

Example 5

ΔN146 is Resistant to IFN

Type I IFN is necessary to prime immunity against a tumor. On the other hand, it mediates antiviral responses. To determine whether ΔN146 is refractory to clearance by IFN, viral growth was examined. As proof of concept, the viral response to IFN was first determined in Vero cells, which are devoid of IFN-α/β genes. Treatment with IFN-α had little effect on replication of HSV-1(F) but drastically reduced replication of Δγ₁34.5 by approximately 1000-fold. However, IFN-α only modestly decreased replication of ΔN146. Furthermore, when tested in 4T1 and MDA-MB-231 cells, a similar trend was observed. While IFN-α reduced viral replication in general, the effect was smaller on wild-type HSV-1 or ΔN146. Indeed, ΔN146 consistently replicated 500- to 1000-fold higher than Δγ₁34.5 in the presence of exogenous IFN-α. Thus, amino-acids 147-263 from γ₁34.5 are sufficient to confer viral resistance to IFN.

Example 6

ΔN146 Reduces Primary Tumor Growth and Metastasis In Vivo

In light of the results presented in Examples 2-5, it was posited that the capacity of ΔN146 to replicate and activate inflammation would enhance tumor destruction in vivo. To demonstrate this, an aggressive 4T1 mammary carcinoma was selected that spontaneously metastasizes, a process analogous to human mammary tumors. For comparison, Δγ₁34.5 was also as it resembles HSV1716 (Rampling, et al. (2000) Gene Ther. 7:859-866; Streby, et al. (2017) Clin. Cancer Res. 23:3566-3574). In addition, recombinant HSV EUs11 (Liu, et al. (2018) J. Virol. 92) was included as this virus is structurally equivalent to the oncolytic backbone for talimogene laherparepvec (Liu, et al. (2003) Gene Ther. 10:292-303). Tumors established subcutaneously in the flank of mice were thrice injected with PBS, Δγ₁34.5, ΔN146 or EUs11 (1×10⁷ pfu) on days 1, 3, and 6. Tumor size was then monitored. As illustrated in FIG. 1, control tumors treated with PBS grew at a faster rate over time. Treatment with γ₁34.5 null virus marginally reduced local tumor growth. However, intra-tumor inoculation with ΔN146 or EUs11 markedly slowed tumor growth and a reduction in tumor size became more apparent as treatment progressed. On day 24, ΔN146 as well as EUs11 reduced the tumor size by nearly 45% as compared to the mock control or Δγ₁34.5. Hence, while comparable to EUs11, ΔN146 displayed superior activity against primary tumors when compared with Δγ₁34.5.

Figure 2:
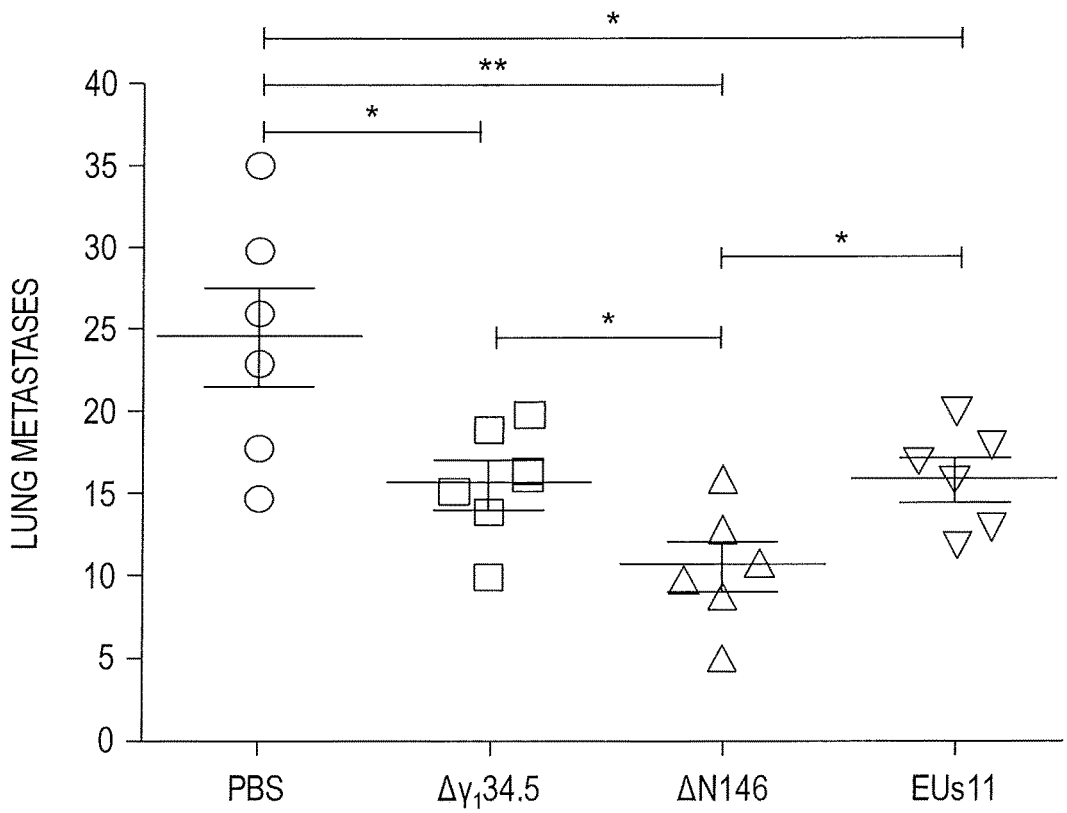
FIG. 2 provides data demonstrating that ΔN146 reduces metastasis. 4T1 cells were implanted subcutaneously into mice (day −7). Tumors formed were injected with PBS, Δγ₁34.5, ΔN146, or EUs11 suspended in PBS on days 1, 3, and 6. Mice were sacrificed on day 24 after the initiation of treatment and the lungs were collected and fixed in formalin. The number of lung metastases was quantified by counting under a light microscope. The results shown are from one of three independent experiments. Differences between the selected groups were statistically assessed by a two-tailed Student t test (*, $P<0.05$; **, $P<0.01$).

To assess the viral impact on metastasis, lung tumor formation was analyzed on day 24. FIG. 2 shows that pulmonary metastasis was readily detectable in control mice, with an average of 25 nodules per animal as measured by microscopic analysis. Treatment with Δγ₁34.5 or EUs11 reduced incidence, with an average of 15 nodules per animal. Notably, ΔN146 further reduced metastatic burden, with an average of 10 nodules. These results indicate that Δγ₁34.5 virus reduces pulmonary metastasis; however, ΔN146 exerted a more pronounced effect.

Example 7

ΔN146 Replicates in Primary Tumor but Not Normal Tissues

Figure 3:
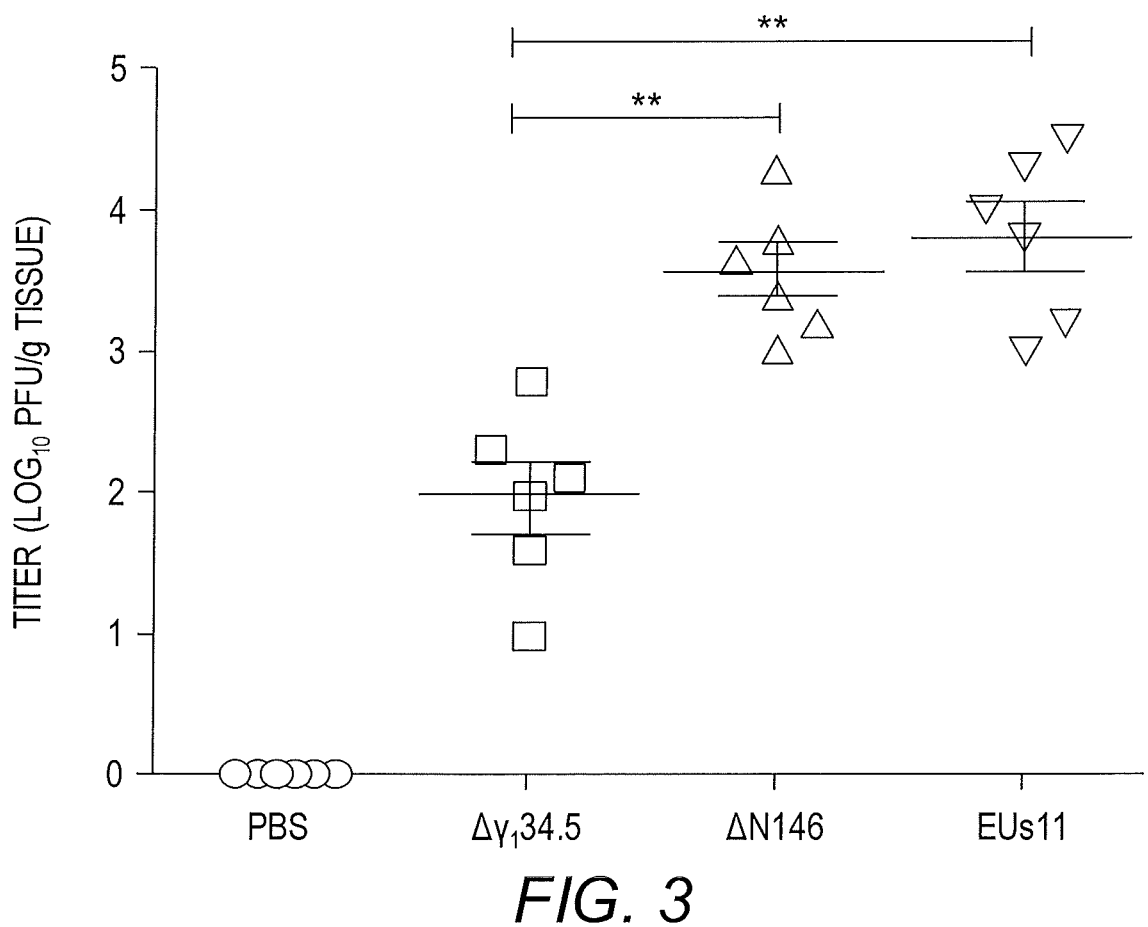
FIG. 3 provides data demonstrating viral growth in 4T1 tumors. Tumors treated with PBS, Δγ₁34.5, ΔN146, or EUs11 suspended in PBS were collected on day 9, and infectious viruses present in tumors were quantified by plaque assay (n=6). The results shown are from three experiments with triplicate samples. Differences between the selected groups were statistically assessed by a two-tailed Student's t-test (**$P<0.01$).

To assess viral replication, viral yields in primary tumors collected on day 9 were determined. This analysis indicated that Δγ₁34.5 replicated at an average titer of 1×10² pfu/g tumor tissue as measured by plaque assay (FIG. 3). On the other hand, EUs11 grew at an average titer of 7×10³ pfu/g tumor tissue. Similarly, ΔN146 grew at an average titer of 5×10³ pfu/g tumor tissue. Apparently, like EUs11, ΔN146 replicated 50-fold better than Δγ₁34.5. In line with this, viral antigens were detected in thin sections of the tumor beds, where ΔN146 and EUs11 spread more extensively than Δγ₁34.5. This correlated with the degree of necrosis of the tumor tissues.

To gauge whether viruses spread to the normal tissues, it was determined whether Δγ₁34.5, ΔN146 and EUs11 were present in the lung, blood, liver and spleen by qPCR assay. This analysis indicated that none of the viruses was detectable in these tissues on day 9 although they were readily found in the tumors. These results indicate that like that of Δγ₁34.5 or EUs11, replication of ΔN146 is limited to the tumor tissues in vivo.

To verify that viral replication indeed occurs actively in the tumors, triple therapy of 4T1 primary tumors was performed and viral yields on day 7, 9 and 15 were measured. This analysis indicated that viruses were detectable at about 2×10² pfu/g tumor tissue on day 7 by plaque assay. As treatment progressed, the quantity of Δγ₁34.5 remained unchanged initially and then reduced to 1×10 pfu/g tumor tissue by day 15. However, under these same conditions, the level of ΔN146 increased to $1\times10^4$ pfu/g tumor tissue on day 9, which subsequently decreased to $1\times10^3$ pfu/g tumor tissue by day 15. EUs11 displayed a similar growth pattern. Therefore, unlike $\Delta\gamma_1 34.5$, ΔN146 as well as EUs11 are able to replicate within tumor in vivo.

Example 8

ΔN146 Induces Infiltration of CD4+ and CD8+ T Cells into the Primary Tumor

Previous evidence suggests that oncolytic HSV with deletion of $\gamma_1 34.5$ activates systemic antitumor immunity (Thomas & Fraser (2003) *Mol. Ther.* 8:543-51; Toda, et al. (1999) *Hum. Gene They.* 10:385-93). As intra-tumor virus injection reduced both local tumor growth and metastasis formation, it was determined whether there was induction of adaptive immunity. As such, CD4+ and CD8+ T cells were assessed by immunohistochemistry analysis. Primary tumors collected on day 24 were thin sectioned and stained for the presence of CD4+ and CD8+ T cells. In mock-infected tumors, a few $CD4^+$ or $CD8^+$ T cells (<4%) were detectable. However, in tumor treated with $\Delta\gamma_1 34.5$, $CD4^+$ T cells rose to 12% and $CD8^+$ T cells to 7%. Similarly, ΔN146 accounted for 15% of $CD4^+$ and 8% $CD8^+$ T cells. Although EUs11 triggered immune cell infiltration, the observed effect was reduced for both $CD4^+$ (10%) and $CD8^+$ T cells (5%).

These results indicate that similar to $\Delta\gamma_1 34.5$, ΔN146 induces T cell infiltration whereas EUs11 appears to dampen this process.

Example 9

ΔN146 and EUs11 Interact with Tumor Cells Differently

Figure 4:
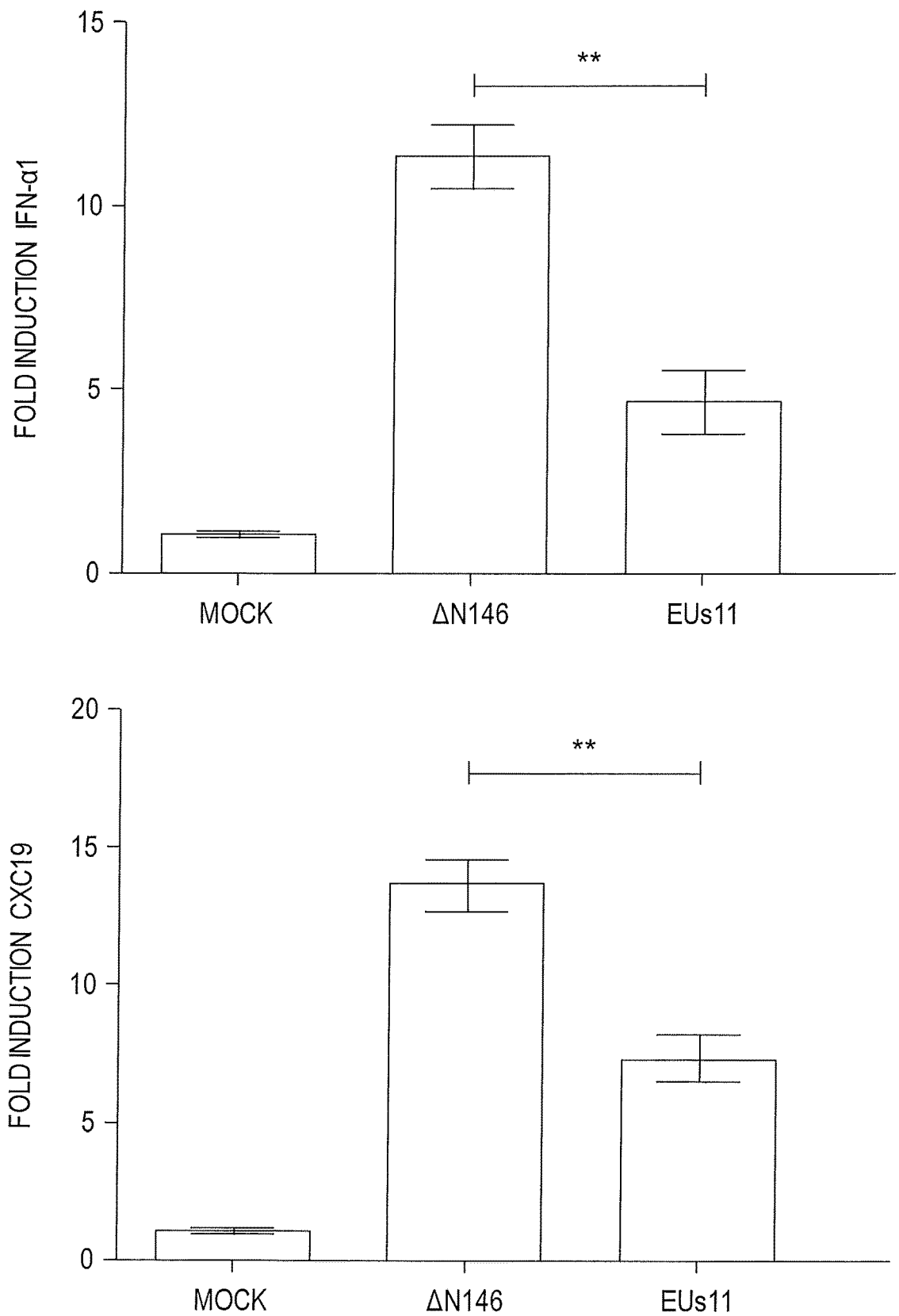
FIG. 4 shows comparative analysis of ΔN146 and EUs11 in vitro. Viral effects on the expression of IFN-α1 and Cxc19 were analyzed. 4T1 cells were mock-infected or infected with ΔN146 or EUs11 (5 pfu/cell). At 6 hours post-infection, RNA samples were analyzed by quantitative polymerase chain reaction. Data are representative of three experiments among triplicate samples with standard deviations.

To determine whether ΔN146 and EUs11 interact with tumor cells differently, in vitro analyses were conducted. As shown in FIG. 4, ΔN146 infection stimulated transcription of IFN-α1 and cxc19 genes. In contrast, EUs11 suppressed gene expression. This paralleled with the levels of cytokine production as measured by ELISA. Consistently, ΔN146 stimulated phosphorylation of IRF3 whereas EUs11 failed to do so, suggesting EUs11 mediates immunosuppression upon virus infection.

To assess the viral capacity to destruct tumor cells, cell viability was measured. This analysis indicated that like EUS11, ΔN146 lysed almost 95% of 4T1 cells by 72 hours. Thus, both ΔN146 and EUs11 lysed tumor cells efficiently. Further, viral replication in 4T1 cells with or without IFN treatment was determined. This analysis indicated that in the absence of IFN-α both ΔN146 and EUs11 replicated efficiently, with a titer reaching about $1\times10^6$ pfu/ml. Addition of exogenous IFN-α modestly reduced viral replication for ΔN146 and EUs11, with a titer of $5\times10^4$ pfu/ml, indicating that they are equally resistant to type I IFN.

---

What is claimed is:

1. A method for treating a subject with breast cancer comprising administering to the subject a therapeutically effective amount of a recombinant Herpes Simplex Virus-1 (HSV-1) that expresses only a $\gamma_1 34.5$ protein consisting of SEQ ID NO:2 with no wild-type or intact $\gamma_1 34.5$ protein expression thereby treating the subject's breast cancer.

2. The method of claim 1, wherein the recombinant HSV-1 further comprises a deletion of one or more non-essential genes or fragments thereof.

3. The method of claim 2, wherein the non-essential genes are selected from UL2, UL3, UL4, UL9.5, UL10, UL11, UL12, UL13, UL14, UL20, UL21, UL23, UL24, UL39, UL40, UL41, UL43, UL43.5, UL44, UL45, UL46, UL47, UL50, UL51, UL53, UL55, Us1, Us1.5, Us2, Us3, Us4, Us5, Us7, Us8, Us8.5, Us9, Us10, Us11, Us12, and ICP0.

4. The method of claim 1, wherein the recombinant HSV-1 further comprises replacement of one or more non-essential genes with one or more genes expressing a therapeutic protein, enzyme, antibody or nucleic acid for cancer therapy.

5. The method of claim 4, wherein the non-essential genes are selected from UL2, UL3, UL4, UL9.5, UL10, UL11, UL12, UL13, UL14, UL20, UL21, UL23, UL24, UL39, UL40, UL41, UL43, UL43.5, UL44, UL45, UL46, UL47, UL50, UL51, UL53, UL55, Us1, Us1.5, Us2, Us3, Us4, 1 Us5, Us7, Us8, Us8.5, Us9, Us10, Us11, Us12, and ICP0.

6. The method of claim 4, wherein the therapeutic protein is selected from interferon alpha, interleukin-2, and granulocyte-colony stimulating factor.

7. The method of claim 4, wherein the antibody is selected from an anti-programmed cell death protein 1 antibody, anti-checkpoints T-lymphocyte-associated protein 4 antibody, anti-Ox40 antibody, and anti-CD40 antibody.

8. The method of claim 1, further comprising administering an effective amount of a second therapeutic agent useful for the treatment of cancer.

* * * * *